United States Patent
Freeman et al.

(10) Patent No.: US 10,219,777 B2
(45) Date of Patent: *Mar. 5, 2019

(54) SYSTEM FOR POSITIONING AN INTUBATION TUBE

(71) Applicant: ZOLL Medical Corporation, Chelmsford, MA (US)

(72) Inventors: Gary A. Freeman, Waltham, MA (US); Ulrich Herken, Medford, MA (US); Annemarie Silver, Bedford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/790,611

(22) Filed: Oct. 23, 2017

(65) Prior Publication Data
US 2018/0146946 A1    May 31, 2018

Related U.S. Application Data

(63) Continuation of application No. 15/080,891, filed on Mar. 25, 2016, now Pat. No. 9,826,956.
(Continued)

(51) Int. Cl.
*A61M 16/04* (2006.01)
*A61B 7/00* (2006.01)
(Continued)

(52) U.S. Cl.
CPC ............. *A61B 7/008* (2013.01); *A61B 7/003* (2013.01); *A61B 7/005* (2013.01); *A61B 7/026* (2013.01);
(Continued)

(58) Field of Classification Search
CPC ......... A61B 7/003; A61B 7/005; A61B 7/008; A61B 7/026; A61M 16/0051; A61M 16/021; A61M 16/0488; A61M 2016/0027; A61M 2016/0036; A61M 2205/332; A61M 2205/3375; A61M 2205/505;
(Continued)

(56) References Cited

U.S. PATENT DOCUMENTS

| | | | |
|---|---|---|---|
| 5,885,248 | A | 3/1999 | Denton |
| 6,164,277 | A | 12/2000 | Merideth |

(Continued)

OTHER PUBLICATIONS

International Search Report and Written Opinion; Application No. PCT/US2016/024166; dated Jun. 27, 2016; 14 pages.
(Continued)

*Primary Examiner* — Ruth S Smith
(74) *Attorney, Agent, or Firm* — Fish & Richardson P.C.

(57) ABSTRACT

This document describes a system for determining positioning of an intubation tube in a patient. The system can include a first acoustic sensor configured to be disposed to listen to one of a lung and a stomach of the patient and to provide a first signal. The system includes a signal processing unit, coupled to the first acoustic sensor, configured to analyze spectral components of the first signal and determine whether a frequency of the spectral components of the first signal are characteristic of sounds induced by ventilation via the intubation tube of airflow to the lung or the stomach of the patient.

20 Claims, 6 Drawing Sheets

Related U.S. Application Data (60) Provisional application No. 62/139,061, filed on Mar. 27, 2015.

(51) Int. Cl.
*A61B 7/02* (2006.01)
*A61M 16/00* (2006.01)

(52) U.S. Cl.
CPC ...... *A61M 16/0051* (2013.01); *A61M 16/021* (2017.08); *A61M 16/0488* (2013.01); *A61M 2016/0027* (2013.01); *A61M 2016/0036* (2013.01); *A61M 2205/332* (2013.01); *A61M 2205/3375* (2013.01); *A61M 2205/505* (2013.01); *A61M 2205/52* (2013.01); *A61M 2230/04* (2013.01); *A61M 2230/205* (2013.01); *A61M 2230/30* (2013.01); *A61M 2230/42* (2013.01); *A61M 2230/50* (2013.01); *A61M 2230/65* (2013.01)

(58) Field of Classification Search
CPC .......... A61M 2205/52; A61M 2230/04; A61M 2230/205; A61M 2230/30; A61M 2230/42; A61M 2230/50; A61M 2230/65; G01N 15/1434; G01N 15/1463; G01N 2015/0065; G01N 2015/1006; G01N 2015/1452; G03H 1/0443; G03H 1/0866; G03H 2001/005; G03H 2001/0428; G03H 2001/0447; G03H 2001/0469; G03H 2001/0883; G06T 2207/10056; G06T 2207/30024; G06T 7/0012

See application file for complete search history.

(56) References Cited

U.S. PATENT DOCUMENTS

| | | |
|---|---|---|
| 6,349,720 B1 | 2/2002 | Clark |
| 9,826,956 B2 * | 11/2017 | Freeman ................ A61B 7/008 |
| 2003/0018276 A1 | 1/2003 | Mansy et al. |
| 2008/0045832 A1 | 2/2008 | McGrath |
| 2009/0036790 A1 | 2/2009 | Landesberg |
| 2014/0180138 A1 | 6/2014 | Freeman et al. |

OTHER PUBLICATIONS

Notification of Transmittal of International Preliminary Report on Patentability for International Application No. PCT/US16/24166 dated Dec. 8, 2016.

* cited by examiner

SYSTEM FOR POSITIONING AN INTUBATION TUBE

CROSS-REFERENCE TO RELATED APPLICATIONS

This application is a continuation application of and claims priority to U.S. Pat. No. 9,826,956, filed on Mar. 25, 2016, which claims priority to U.S. Provisional Application Serial No. 62/139,061 filed on Mar. 27, 2015, entitled "SYSTEMS AND METHODS FOR POSITIONING AN INTUBATION TUBE." Each application is incorporated herein by reference.

TECHNICAL FIELD

This document describes systems and methods for determining placement of an intubation tube in a patient.

BACKGROUND

Tracheal intubation is a procedure performed on patients who are unconscious or otherwise cannot breathe on their own. The placement of an endotracheal tube in the trachea of the patient helps prevent suffocation or obstruction of the passage of air to the lungs and serves as a conduit through which medication can be administered. Typically, intubation is performed with a laryngoscope, flexible fiber-optic bronchoscope, or video laryngoscope. After insertion of the intubation tube, a balloon cuff at the far end of the tube is inflated to secure placement of the tube.

Although intubation provides relief in emergency situations, or situations in which a patient cannot breathe under her own power, there are considerable dangers associated with tracheal intubation. For example, placement of the tube in the esophagus of the patient can lead to potentially fatal anoxia. Furthermore, improper placement of the tube relative to the carina can result in unevenly ventilated lungs. When properly positioned, the distal tip of the tube will be positioned in the mid-trachea slightly above the bifurcation of the trachea. Conventional methods for addressing placement of the intubation tube include direct visualization until the tube passes through the glottis of the patient and indirect visualization using a bronchoscope after visual contact is lost. Additional techniques include listening to the chest and stomach with a stethoscope.

SUMMARY

This document describes a first acoustic sensor configured to be disposed to listen to one of a lung and a stomach of the patient and to provide a first signal, and a signal processing unit, coupled to the first acoustic sensor, configured to analyze spectral components of the first signal and determine whether a frequency of the spectral components of the first signal are characteristic of sounds induced by ventilation via the intubation tube of airflow to the lung or the stomach of the patient. The function of the preamble is to set forth the general technical environment of the invention.

In some implementations, the signal processing unit is further configured to provide an instruction to relocate the first acoustic sensor responsive to the determination. The signal processing unit is further configured to provide an instruction to relocate the first acoustic sensor at one of a third left intercostal region, a third right intercostal region, a sixth left intercostal region, a sixth right intercostal region, and a stomach region of the body of the patient. In some implementations, the actions include a second acoustic sensor configured to be disposed to listen to one of the lung and the stomach of the patient and to provide a second signal, wherein the signal processing unit is further coupled to the second acoustic sensor and configured to analyze spectral components of the second signal and determine whether a frequency of the spectral components of the second signal are characteristic of sounds induced by ventilation via the intubation tube of airflow to the lung or the stomach of the patient. In some implementations, the signal processing unit is further configured to determine whether an amplitude of the spectral components of the first signal and the second signal are substantially equal, and provide an instruction to relocate a position of the intubation tube in the patient in response to a determination that the amplitude of the spectral components of the first signal and the second signal are substantially unequal. In some implementations, the first acoustic sensor is configured to be disposed at approximately the third left intercostal region of the body of the patient, and the second acoustic sensor is configured to be disposed at approximately the third right intercostal region of the body of the patient. In some implementations, the actions include a third acoustic sensor coupled to the signal processing unit and configured to be disposed at approximately the stomach region of the body of the patient and to provide a third signal, wherein the signal processing unit is further configured to analyze spectral components of the third signal. In some implementations, the signal processing unit is further configured to analyze spectral components of the third signal and determine whether a frequency of the spectral components of the third signal are characteristic of sounds induced by ventilation via the intubation tube of airflow to the stomach of the patient. The actions include an air flow sensor configured to detect airflow through the intubation tube; wherein the signal processing unit is coupled to the air flow sensor and further configured to analyze the spectral components of the first signal responsive to detecting the airflow through the intubation tube. In some implementations, the air flow sensor is positioned at a distal tip of the intubation tube. In some implementations, the air flow sensor is positioned at a proximal tip of the intubation tube. In some implementations, the air flow sensor includes a differential air flow sensor. The actions include a first pressure sensor positioned at a proximal tip of the intubation tube; and a second pressure sensor positioned at the distal tip of the intubation tube; wherein the signal processing unit is coupled to the first pressure sensor and the second pressure sensor and configured to analyze a pressure differential between a first pressure detected by the first pressure sensor and a second pressure detected by the second pressure sensor. The signal processing unit is further configured to filter vibrational noise transduced into the first signal from chest compressions delivered to the patient.

In some implementations, the system includes a first acoustic sensor configured to be disposed to listen to one of a lung and a stomach of the patient and to provide a first signal; a second acoustic sensor configured to be disposed to listen to one of the lung and the stomach of the patient and to provide a second signal; and a signal processing unit, coupled to the first acoustic sensor and the second acoustic sensor, configured to analyze spectral components of the first signal and the second signal, and determine that the intubation tube is properly disposed in the body of the patient in response to a determination that a frequency of the spectral components of the first signal and the second signal are characteristic of sounds of airflow to the lung or the stomach of the patient.

In some implementations, the signal processing unit is further configured to determine whether the frequency of the spectral components of the first signal and second signal are above a determined threshold and an amplitude of the spectral components of the first signal and the second signal are substantially equal, and determine that the intubation tube is properly disposed in the body of the patient in response to a determination that the frequency of the spectral components of the first signal and the second signal are above the determined threshold and the amplitude of the spectral components of the first signal and the second signal are substantially equal. The actions include an air flow sensor configured to detect airflow through the intubation tube; wherein the signal processing unit is coupled to the air flow sensor and further configured to analyze the spectral components of the first signal and the second signal responsive to detecting the airflow through the intubation tube. In some implementations, the air flow sensor is positioned at a distal tip of the intubation tube. In some implementations, the air flow sensor is positioned at a proximal tip of the intubation tube. In some implementations, the air flow sensor includes a differential air flow sensor. In some implementations, the actions include a first pressure sensor positioned at a proximal tip of the intubation tube; and a second pressure sensor positioned at the distal tip of the intubation tube; wherein the signal processing unit is coupled to the first pressure sensor and the second pressure sensor and configured to analyze a pressure differential between a first pressure detected by the first pressure sensor and a second pressure detected by the second pressure sensor. In some implementations, the signal processing unit is further configured to filter vibrational noise transduced into the first signal from chest compressions delivered to the patient. In some implementations, the first acoustic sensor and second acoustic sensor each includes one of a microphone and an accelerometer. In some implementations, the first acoustic sensor is disposed in a sensor assembly that includes a first ECG electrode removably coupled to the first acoustic sensor. In some implementations, the sensor assembly includes a self-adhesive pad configured to attach to the body of the patient, and wherein the first ECG electrode and the first acoustic sensor are mounted to the adhesive pad. The adhesive pad includes a perforation disposed between the first ECG electrode and the first acoustic sensor. In some implementations, the signal processing unit is further configured to analyze the first signal and the second signal and determine displacement of the body in the third left intercostal region and the third right intercostal region. In some implementations, the signal processing unit is further configured to compare the displacement of the body in the third left intercostal region and the third right intercostal region, and to determine that the intubation tube is properly disposed in the body of the patient in response to the determination that the frequency of the spectral components of the first signal and the second signal are above the determined threshold and the amplitude of the spectral components of the first signal and the second signal are substantially equal, and determining that the displacement of the body in the third left intercostal region is substantially equal to the displacement of the body in the third right intercostal region. In some implementations, the signal processing unit is further configured to low-pass filter the first signal and the second signal prior to analyzing the first signal and the second signal and determining displacement. In some implementations, the signal processing unit is configured to low-pass filter the first signal and the second signal with a pass-band of 0 Hz to 5 Hz. The signal processing unit is further configured to band-pass filter the first signal and the second signal prior to analyzing the spectral components of the first signal and the second signal. The signal processing unit is configured to band-pass filter the first signal and the second signal with a pass-band of 5 Hz to 5000 Hz.

The signal processing unit is further configured to analyze the first signal and the second signal and determine displacement of the body in the third left intercostal region and the third right intercostal region. In some implementations, the signal processing unit is further configured to compare the displacement of the body in the third left intercostal region and the third right intercostal region, and to determine that the intubation tube is properly disposed in the body of the patient in response to the determination that the frequency of the spectral components of the first signal and the second signal are above the determined threshold and the amplitude of the spectral components of the first signal and the second signal are substantially equal, and determining that the displacement of the body in the third left intercostal region is substantially equal to the displacement of the body in the third right intercostal region. In some implementations, the actions include a third acoustic sensor coupled to the signal processing unit and configured to be disposed at approximately the left abdominal region of the body of the patient and to provide a third signal; and a fourth acoustic sensor coupled to the signal processing unit and configured to be disposed at approximately the right abdominal region of the body of the patient and to provide a fourth signal; wherein the signal processing unit is further configured to analyze spectral components of the third signal and the fourth signal, determine whether a frequency of the spectral components of the third signal and the fourth signal are above the determined threshold and an amplitude of the spectral components of the third signal and the fourth signal are substantially equal, and determine that the intubation tube is properly disposed in the body in response to the determination that the frequency of the spectral components of the first signal, the second signal, the third signal, and the fourth signal are above the determined threshold, the amplitude of the spectral components of the first signal and the second signal are substantially equal, and the amplitude of the spectral components of the third signal and the fourth signal are substantially equal. In some implementations, the third acoustic sensor and the fourth acoustic sensor each includes one of a microphone and an accelerometer. In some implementations, each of the first, second, third, and fourth acoustic sensors is disposed in a sensor assembly that includes a respective ECG electrode. The actions include a fifth acoustic sensor coupled to the signal processing unit and configured to be disposed at approximately the stomach region of the body of the patient and provide a fifth signal; wherein the signal processing unit is further configured to analyze spectral components of the fifth signal.

The system performs actions including receiving a first signal from a first acoustic sensor disposed to listen to one of a lung and a stomach of the patient; receiving a second signal from a second acoustic sensor disposed to listen to one of the lung and the stomach of the patient; comparing a frequency of spectral components of the first signal and the second signal to sounds of airflow to the lung or the stomach of the patient; and determining positioning of the intubation tube in a body of the patient in response to the comparison of the frequency of the spectral components.

In some implementations, performs actions including comparing the frequency of the spectral components of the first signal and the second signal comprises comparing the frequency of the spectral components of the first signal and the second signal to a determined threshold. The actions include comparing an amplitude of the spectral components of the first signal and the second signal; and determining positioning of the intubation tube in the body of the patient in response to the comparison of the amplitude and the comparison of the frequency. The actions include receiving a first ECG signal from a first ECG electrode removably coupled to the first acoustic sensor and receiving a second ECG signal from a second ECG electrode removably coupled to the second acoustic sensor. The actions include analyzing the first signal and the second signal; and determining displacement of the body in a third left intercostal region and a third right intercostal region. The actions include comparing the displacement of the body in the third left intercostal region and the third right intercostal region, and determining that the intubation tube is properly disposed in the body of the patient in response to determining that the frequency of the spectral components of the first signal and the second signal are above the determined threshold, the amplitude of the spectral components of the first signal and the second signal are substantially equal, and the displacement of the body in the third left intercostal region is substantially equal to the displacement of the body in the third right intercostal region. In some implementations, the actions include low-pass filtering the first signal and the second signal prior to analyzing the first signal and the second signal and determining displacement. In some implementations, the act of low-pass filtering includes filtering the first signal and the second signal with a pass-band of 0 Hz to 5 Hz. The actions include band-pass filtering the first signal and the second signal prior to comparing the frequency of the spectral components of the first signal and the second signal to a determined threshold. In some implementations, the act of band-pass filtering includes band-pass filtering the first signal and the second signal with a pass-band of 5 Hz to 5000 Hz. The actions include analyzing the first signal and the second signal; and determining displacement of the body in a third left intercostal region and a third right intercostal region. In some implementations, the actions include comparing the displacement of the body in the third left intercostal region and the third right intercostal region, and determining that the intubation tube is properly disposed in the body of the patient in response to determining that the frequency of the spectral components of the first signal and the second signal are above the determined threshold, an amplitude of the spectral components of the first signal and the second signal are substantially equal, and the displacement of the body in the third left intercostal region is substantially equal to the displacement of the body in the third right intercostal region. In some implementations, the actions include receiving a third signal from a third acoustic sensor disposed at approximately the left abdominal region of the body of the patient; receiving a fourth signal from a fourth acoustic sensor disposed at approximately the right abdominal region of the body of the patient; comparing an amplitude of spectral components of the third signal and the fourth signal; comparing a frequency of the spectral components of the third signal and the fourth signal to a determined threshold; and determining positioning of the intubation tube in the body of the patient in response to the comparison of the amplitude and the comparison of the frequency. In some implementations, the actions include analyzing the third signal and the fourth signal; and determining displacement of the body in the left stomach region and the right stomach region. In some implementations, the actions include receiving a third ECG signal from a third ECG electrode removably coupled to the third acoustic sensor and receiving a fourth ECG signal from a fourth ECG electrode removably coupled to the fourth acoustic sensor. The actions include receiving a fifth signal from a fifth acoustic sensor disposed at approximately the stomach region of the body of the patient; and analyzing spectral components of the fifth signal. In some implementations, the actions include triggering the act of comparing the frequency of spectral components of the first signal and the second signal to sounds of airflow to the lung or the stomach of the patient responsive to detecting airflow through the intubation tube. In some implementations, the actions include triggering the act of comparing the frequency of spectral components of the first signal and the second signal to sounds of airflow to the lung or the stomach of the patient responsive to detecting a pressure differential between a first pressure sensor positioned at a proximal tip of the intubation tube and a second pressure sensor positioned at a distal tip of the intubation tube.

DETAILED DESCRIPTION

This document describes methods and systems to facilitate placement of an endotracheal intubation tube. An intubation tube positioning system determines placement of an intubation tube in a patient such that human error in auditorily comparing respiration and stomach sounds can be avoided. Once the intubation tube is placed in the patient, the positioning system can monitor the position of the intubation tube to verify that the placement of the intubation tube is maintained.

As discussed above, to determine proper placement of endotracheal intubation tubes conventional methods utilize direct visualization, indirect visualization via a bronchoscope, or typically, physician placed stethoscopes. Accordingly, these methods recognize that a properly placed intubation tube will result in equilateral breathing sounds, and minimal noise in the stomach region of the patient. Nevertheless, these methods require a highly trained physician to recognize the sounds of a properly placed intubation tube. Often the distinction in sounds is difficult to recognize by ear and subject to interference created by environmental conditions such as patient movement and ambient noise.

Applicants have appreciated there is a need to facilitate proper placement of an endotracheal intubation tube and protect patients from improperly placed intubation tubes. To address these needs, Applicants have developed a number of different embodiments of an intubation tube positioning system that determines proper placement of an intubation tube in a patient while removing the human error in auditorily comparing respiration and stomach sounds. Once the intubation tube is properly placed in the patient, embodiments of the present system can also monitor the position of the intubation tube to verify that proper placement of the intubation tube is maintained.

Figure 1A:
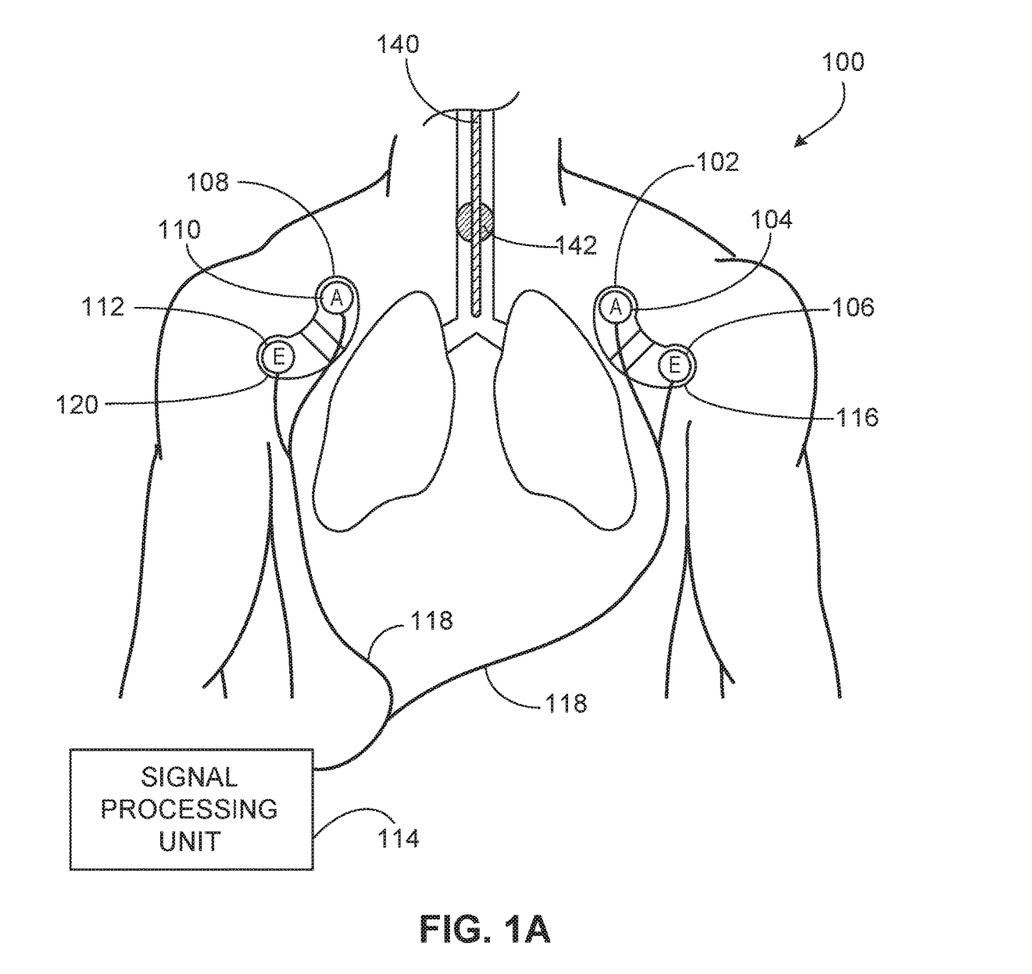
FIGS. 1A-1B show examples of intubation tube placement systems.

FIG. 1A shows an example of an intubation tube positioning system 100. The intubation tube positioning system 100 includes an intubation tube 140. The intubation tube 140 includes a balloon cuff 142 disposed at its distal end to maintain the position of the tube 140 in the trachea and create a seal with the trachea wall. The intubation tube positioning system 100 includes a first sensor assembly 102 having an acoustic sensor 104, a second sensor assembly 108 having an acoustic sensor 110, a plurality of connectors 118, and a signal processing unit 114. In some implementations, the first sensor assembly 102 is configured to be disposed at approximately the third left intercostal region of the body of the patient and the second sensor assembly 108 is configured to be disposed at approximately the third right intercostal region of the body of the patient. The intercostal region is the anatomic space between two ribs. For example, the third left intercostal region corresponds to the left side of the patient between ribs three and four and the third right intercostal region corresponds to the right side of the patient between ribs three and four. In some implementations, the first assembly 102 and second assembly 108 are placed slightly above the nipple and below the clavicle. In some implementations the sensor assemblies 102, 108 are displaced in the third intercostal regions of the body. In some implementations, the sensor assemblies 102, 108 are configured to be disposed in other regions of the patient's body.

As shown in FIG. 1A, the first sensor assembly 102 includes an acoustic sensor 104 and the second sensor assembly 108 includes an acoustic sensor 110. Various types of acoustic sensors can be used, such as the AUDICOR™ RT 4.0 AM sensor and similar sensors provided by Inovise Medical, Inc., and other acoustic sensors described in greater detail below. The acoustic sensors can include an accelerometer, microphone, or other additional sensors. The acoustic sensors are configured to detect and convey acoustic signals, such as those created by activity (e.g., movement) of the lungs or stomach of the patient. The acoustic sensors are interconnected, via the connection element 118, to the signal processing unit 114 and may exchange data such as collected acoustic signals. The connection element 118 can include a pair of leads extending from the acoustic sensors to the signal processing unit 114. In some implementations, the first and second sensor assemblies can further include a battery operatively connected to the acoustic sensors and configured provide electrical power for signal detection operations.

In some implementations, the acoustic sensor 110 can comprise a three axis multiple-channel MEMS accelerometer. The acoustic sensor 110 may comprise a three-channel accelerometer. In some implementations, a first channel of the three-channel accelerometer is configured to monitor sounds produced by a heart of the patient, a second channel of the three-channel accelerometer is configured to monitor a respiration of the patient, and a third channel of the three-channel accelerometer is configured to monitor movement of the patient. The acoustic three-channel accelerometer can be configured to sense movement in each of three orthogonal axes. An example of an accelerometer which may be utilized in some implementations is a LIS344ALH accelerometer, available from STMicroelectronics.

In some implementations the acoustic sensor 110 comprises a microphone. In some implementations the acoustic sensor 110 comprises an accelerometer. The acoustic sensor 110 and associated electronics may be configured to monitor any one or more of a patient's respiration, a patient's heart sounds, a patient's position, and an activity level of a patient. The acoustic sensor 110 and associated electronics may additionally or alternatively be configured to monitor other sounds which may be indicative of a state of health of a patient, for example, gastrointestinal sounds or the sounds of snoring or the absence of such sounds, for example, to provide an indication of the patient experiencing sleep apnea. The acoustic sensor 110 may provide signals indicative of the patient's respiration on a first channel, signals indicative of the patient's heart sounds on a second channel, and signals indicative of the patient's position on a third channel. In other implementations, the different channels may be utilized to provide signals indicative of more than one physiological parameter or other parameter associated with the state of the patient. For example, in one implementation, the acoustic sensor 110 may provide signals indicative of the patient's heart sounds on a first channel, signals indicative of the patient's respiration on a second channel, and signals indicative of the patient's body position on any or all of the first, second, and third channel. It should be appreciated that dependent on the underlying parameter that is being monitored, multiple signals related to the parameter being monitored may be received over a single channel or a number of different channels.

Further, when including an accelerometer, the acoustic sensor 110 and associated electronics may be configured to provide an indication of whether a therapy electrode assembly including the acoustic sensor has been correctly placed on a patient. The acoustic sensor 110 and associated electronics may be configured to detect, for example, by sensing the direction of the pull of the Earth's gravity, the orientation of the acoustic sensor 110, and of the therapy electrode assembly in which it is included. The acoustic sensor 110 and associated electronics may thus be utilized to provide an indication of whether the therapy electrode assembly has been correctly placed on a patient or whether it has been incorrectly placed, for example, in an inverted position.

The acoustic sensor 110 and associated electronics may be configured to detect whether CPR is being performed on the patient and to output a signal responsive to the detection of the performance of CPR. Further, electronics associated with the acoustic sensor 110 may be configured to analyze the motion associated with the performance of CPR, for example, the rate and depth of chest compressions. Other acoustic sensors can be used, such as those described in U.S. Pat. Nos. 7,302,290, 7,668,589, and 8,409,108, and U.S. Patent Application Ser. No. 2015/0005588, titled "THERAPUTIC DEVICE INCLUDING ACOUSTIC SENSOR," which are each incorporated herein by reference in entirety.

The signal processing unit 114 can be used to determine and identify the source of the signal being received from the acoustic sensor 110. The acoustic sensor 110 of the intubation tube placement system 100 can be placed on the exterior of the patient and can be used for lung auscultation. The acoustic sensor 110 can be used for detecting lung sounds and tracheal sounds. The signal processing unit can be configured to distinguish between the lung sounds and the tracheal sounds and assist a physician in determining a condition of a patient by making this initial determination, which can change the analysis of the physician since a sound can have different implications for the condition of the patient depending on the source of the sound.

For example, a typical tracheal sound is hollow and nonmusical and can be heard during the two phases of the respiratory cycle. The tracheal sound signal waveform can appear similar to white noise. The frequencies of the tracheal sound can range from about 100 Hz to almost 5000 Hz, but have a drop in power at frequencies near 800 Hz. The tracheal sound can be produced by turbulent airflow in the pharynx, glottis, and subglottic region. The tracheal sound can carry sound from within the lungs, allowing auscultation of other sounds without filtering from the chest cage. For example, if a patient has upper-airway obstruction, the tracheal sound can become a tracheal wheeze, which can be distinguished from asthmatic sounds from the lungs. In addition, tracheal sounds can more easily reveal the presence of bronchial or tracheal stenosis or a tumor in the central airway than the lung sound.

The lung sound is typically soft, nonmusical, and heard clearly during inspiration and during the early phase of expiration. The lung sound signal waveform can appear similar to low-pass filtered noise. The frequency range for the lung sounds is narrower than for the tracheal sounds and extends from about 100 Hz to 1000 Hz, and have a drop in power at frequencies near 100-200 Hz. A decrease in sound intensity is the most common abnormality and can indicate conditions including hypoventilation, airway narrowing, lung destruction, pleural effusion, and pneumothorax. Addition information on characterizing the lung sounds and the tracheal sounds can be found in Bohandana, Abraham, *Fundamentals of Lung Auscultation*, N. Engl. J. Med. 2014; 370:744-51, which is incorporated herein by reference in its entirety.

The signal processing unit 114 can distinguish between the tracheal sound and the lung sound by applying signal processing techniques, described in further detail below. In some implementations, the waveform of a sound that is measured by the acoustic sensor 110 can be analyzed to determine frequency, power, and timing of the signal as compared to the respiratory cycle of the patient to determine the source of the sound and identify the sound as the tracheal sound or the lung sound. For example, a waveform having a frequency of 500 Hz at a given power level can indicate a tracheal source. For example, a waveform having a frequency of 50 Hz at a given power level that is detected during inspiration but not expiration can indicate a lung source.

In addition to the signal processing techniques described above, the signal processing unit 114 can process and analyze tracheal sounds, lung sounds, and other respiratory sounds received by the acoustic sensor 110 using other algorithms and techniques. In some implementations, the acoustic sensors 110 can be multi-axis sound sensors. The acoustic sensors 110 collect several signals from the patient simultaneously along multiple, angularly intersecting X, Y, Z sound-collecting axes. In some implementations, processed signals are supplied that relate (to each other) simultaneously gathered sound signals, including what are referred to herein as processed-output apexcardiogram signals. The processed signals may be created in the contest of having used the X and Y components of collected sound information, including appropriate ratios of X and Y signals, to minimize interference from ambient noise signals, and/or to give information, at the time of signal collection, about how to shift the relevant sound sensor laterally on the anatomy so as to collect the maximum available Z-axis sound signal, a process known as "lateral shifting." In some implementations, X and Y sound components can additionally be employed to detect and characterize shear/surface sound waves for various purposes, such as for the minimizing of extraneous noise interference. In some implementations, the received signals are processed to obtain associated vector magnitude and directionality information. The signals are analyzed using vector magnitude and directionality information for assessment of the subject's condition. These signal processing techniques can be used with acoustic sensors such as the AUDICOR™ RT 4.0 AM sensor and similar sensors provided by Inovise Medical, Inc. Other signal processing techniques can be used, such as those described in U.S. Pat. Nos. 7,302,290, 7,668,589, and 8,409,108, and U.S. Patent Application Ser. No. 2015/0005588, titled "THERAPUTIC DEVICE INCLUDING ACOUSTIC SENSOR," which are each incorporated herein by reference in entirety.

As shown in FIG. 1A, the first sensor assembly 102 and the second sensor assembly 108 additionally include an ECG (electrocardiogram) electrode. A combined sensor assembly that includes both an acoustic sensor and an ECG electrode can be configured to monitor the patient's ECG signals. In some implementations, the ECG signals can be combined with collected acoustic signals. In some implementations, a patient undergoing intubation can have his ECG signals monitored. In the implementation depicted in FIG. 1A, the ECG electrode 106 of the first sensor assembly 102 and the ECG electrode 112 of the second sensor assembly 108 are proximate the first and second acoustic sensors and removably coupled to the first and second acoustic sensors, respectively. In some implementations, each sensor assembly can include a disconnect/connect assembly that separates the acoustic sensor from the respective ECG electrode (e.g., acoustic sensor 104 separates from ECG electrode 106). In some implementations, in each sensor assembly, the acoustic sensor may be removably coupled to the ECG electrode using a hook and loop (e.g., VELCRO®) type fastener, perforated pad, or separable buckle. The ECG electrodes may contact the skin of the patient directly, or via an adhesive pad. The ECG electrodes can measure and record the electrical activity of the heart over a period of time. In some implementations, each ECG electrode is interconnected, via the connection element 118, with the signal processing unit 114 and can exchange data such as the detected ECG signals. In some implementations, the ECG electrodes of the first sensor assembly 102 and second sensor assembly 108 include extensions of ECG leads.

Although shown in FIG. 1A as lying along separate detection axes, in some implementations, the first sensor assembly 102 and the second sensor assembly 108 can include an acoustic sensor and an ECG electrode aligned with one another (e.g. symmetrically aligned) at spaced locations distributed on and along a shared detection axis. In some implementations, the acoustic sensor and ECG electrode may share a common axis with the ECG electrode being disposed within a circumference of the acoustic sensor, as described in U.S. Pat. No. 7,010,342, for example. In this regard, ECG signals that are collected by the ECG electrodes can be treated as emanating from the same source.

In some implementations, when the first sensor assembly 102 and second sensor assembly 108 are placed on the body of the patient for signal collection, the contacting surface of the sensor assembly and corresponding individual sensor(s) includes a conductive gel, which seals the space from outside air and provides an improved electrical and acoustic connection. The conductive gel can further restrict the collected signals to those that are related to the placement site. In some implementations, the first and second sensor assemblies include a self-adhesive pad (pad 116 and pad 120) for traction against the patient's body. The self-adhesive pads 116, 120 stabilize the sensor assemblies 102, 108 against the patient, maintain placement of the sensor assemblies 102, 108 at the signal collection site, and prevent slippage of the sensor assemblies 102, 108 during the course of the intubation process.

As described above, signals from the body detected by the acoustic sensor and ECG electrode of the first sensor assembly 102 and second sensor assembly 108 can be received at the signal processing unit 114. In some implementations, the sensor assemblies 102, 108 include internal acoustic and electric signal processing circuitry such as buffers, amplifiers, and/or analog to digital converters. Signals detected by the acoustic sensors and ECG electrodes shown in FIG. 1A can be received by the signal processing unit 114. In some implementations, the signal processing unit 114 includes acoustic signal processing circuitry and ECG signal processing circuitry. The signal processing unit 114 is configured to determine placement of the intubation tube in the body of the patient in response to analyzing the acoustic and/or the electrical signals received from the first sensor assembly 102 and second sensor assembly 108. Spectral components of lung and stomach sounds can vary vastly in regard to placement of the intubation tube. The signal processing unit 114 compares spectral components of the acoustic signals measured by the first sensor assembly 102 and second sensor assembly 108 with spectral components of lung and esophageal sounds. For example, the sound of aspirating lungs can be of a higher frequency than spectral components of stomach noises. Accordingly, the signal processing unit 114 is configured to compare spectral components of the acoustic signal collected by the first sensor assembly 102 and the acoustic signal collected by the second sensor assembly 108 with a predetermined threshold to determine placement of the intubation tube in the trachea. The predetermined threshold can be indicative of the discrepancy in lung and esophageal spectral components. In some implementations, if the spectral components exhibit a frequency component above the predetermined threshold, the signal processing unit 114 can indicate to an operator of the system 100 (e.g., a clinician) that the intubation tube has been properly placed in the trachea. In some implementations, if the frequency characteristics of the spectral components fall below the predetermined threshold, the signal processing unit 114 indicates or conveys an alert that the intubation tube has been improperly placed in the esophagus. Proper placement of the intubation tube can occur if the intubation tube is placed in a position such that the intubation tube is effective (e.g., positioned according to design specifications). In some implementations, the predetermined threshold can be determined based on patient age, gender, height, weight, and/or physical condition. In some implementations, the threshold value can be a discrete value. In some implementations, the threshold value can include a range of frequencies.

In some implementations, the signal processing unit 114 can also determine placement of the distal end of the intubation tube relative to the carina in response to analysis of the spectral components of acoustic signals collected by the first sensor assembly 102 and second sensor assembly 108. The signal processing unit 114 is configured to compare an amplitude of the spectral components of the signal received from the first sensor assembly 102 to an amplitude of the spectral components of the signal received from the second sensor assembly 108. Because a properly placed intubation tube approximately evenly inflates each lung, substantially equal amplitudes indicate that the tube has been properly positioned.

Referring again to FIG. 1A, the signal processing unit 114 can determine displacement of the body of the patient from detected signal data provided by the first acoustic sensor 104 and the second acoustic sensor 108. In some implementations, when the intubation tube is properly placed in the trachea, the chest of the patient can rise. In some implementations, if the intubation tube is improperly placed in the esophagus of the patient, the abdomen can rise. The signal processing unit 114 can be configured to determine whether a slow level DC component of displacement is occurring, and determine if the intubation tube has been properly placed. In some implementations, the signal processing unit 114 can be configured to convey notice of proper placement of the intubation tube or convey an alert when the intubation tube has been improperly placed.

In some implementations, the signal processing unit 114 includes a band pass filter having a passband of approximately 20 Hz to 5000 Hz for filtering the detected acoustic signals and a low pass filter of about 0 Hz to 5 Hz for the displacement correlated acoustic signals. The disclosed filters can remove unwanted interference such as ambient noise. In some implementations, various filters of the signal processing unit 114 may be configured to filter vibrational noise transduced into the acoustic sensors resulting from chest compressions delivered to the patient. The acoustic sensors may utilize an accelerometer to sense vibration on the chest wall at the sensor assemblies. The same type of accelerometer may be used to measure compression depth by placing it on the patient's sternum underneath hands of an operator (e.g., clinician). In some implementations, filtering is accomplished by blanking the acoustic signal during periods when compressions are detected by the signal processing unit using the signal from the sternal accelerometer.

Figure 1B:
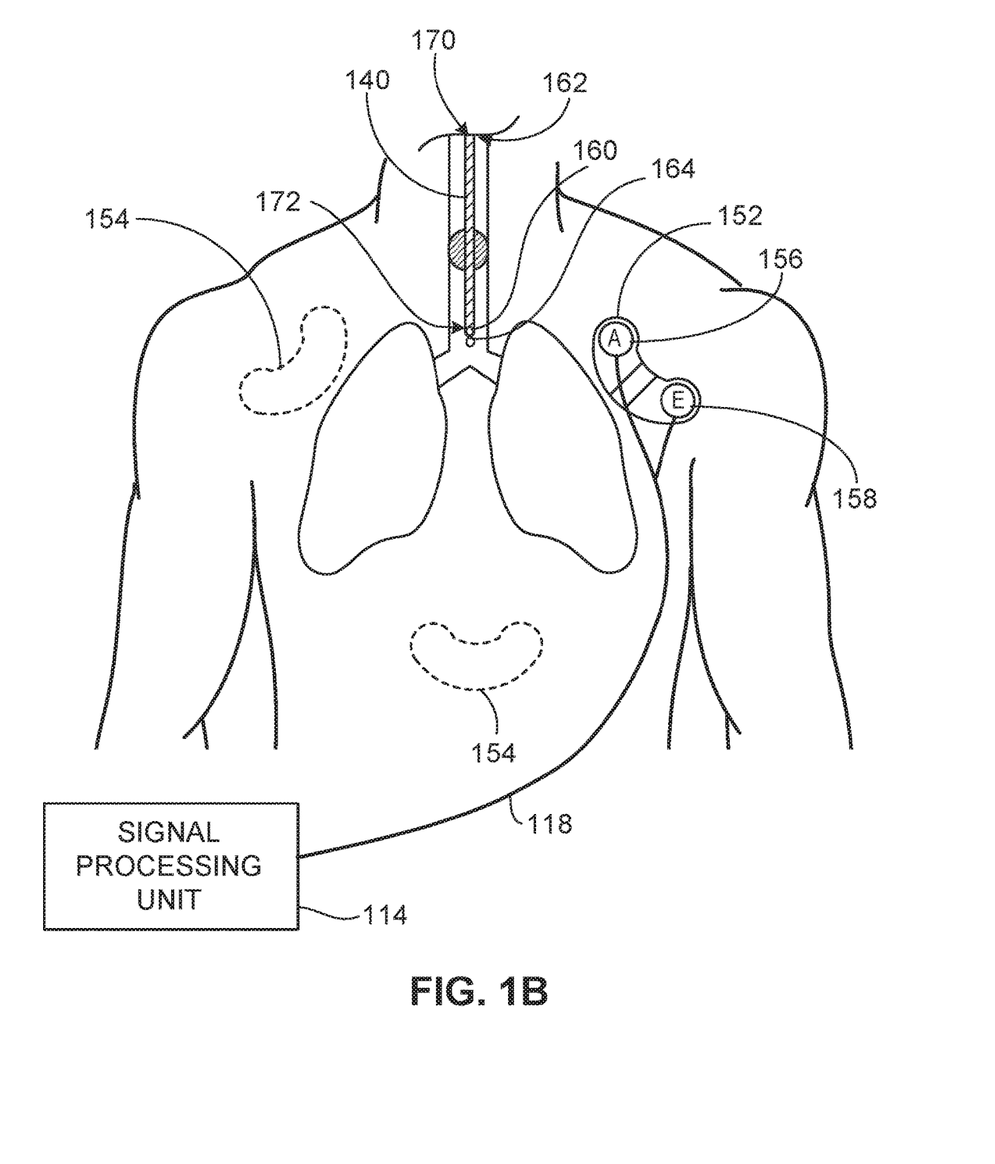

In some implementations the system 100 may include a single sensor assembly. FIG. 1B shows an example intubation tube positioning system 100 including a single sensor assembly 152. In some implementations, the single sensor assembly 152 includes one of the first sensor assembly 102 or second sensor assembly 108. In some implementations, the signal processing unit 114 may be configured to guide placement of the single sensor assembly 152 at various locations of the patient's body (e.g., as indicated generally by ghost lines 154). As shown in FIG. 1B, one implementation of the single sensor assembly 152 includes an acoustic sensor 156. In some implementations, the single sensor assembly 152 is configured to be disposed to listen to one of the lungs or the stomach of the patient. This may include a position at approximately the third left intercostal region of the body of the patient, the third right intercostal region of the body of the patient, or the stomach region of the body of the patient. In some implementations, the single sensor assembly 152 is configured to be displaced in the third intercostal regions of the body. In some implementations, the single sensor assembly 152 can be configured to be disposed in other regions of the patient's body.

As discussed above with reference to the first sensor assembly 102 and second sensor assembly 108, the single sensor assembly 152 is configured to detect and convey acoustic signals, such as those created by activity (e.g., movement) of the lungs or stomach of the patient. The acoustic sensor 156 is interconnected, via the connection element 118, to the signal processing unit 114 and may exchange data such as collected acoustic signals. In some implementations, the single sensor assembly 152 can include an ECG (electrocardiogram) electrode 158. A combined sensor assembly that includes both an acoustic sensor and an ECG electrode can monitor the patient's ECG signals. In some implementations, the ECG signals can be combined with collected acoustic signals. In some implementations, the patients undergoing intubation can have their ECG signals monitored. In some implementations, the single sensor assembly 152 is placed on the body of the patient for signal collection processes and analyses.

As described above, signals from the body detected by the acoustic sensor 156 and ECG electrode 158 of the single sensor assembly 152 can be received at the signal processing unit 114. In some implementations, the single sensor assembly 152 includes internal acoustic and electric signal processing circuitry such as buffers, amplifiers, and/or analog to digital converters. Signals detected by the acoustic sensor 156 and ECG electrode 158 shown in FIG. 1B can be received by the signal processing unit 114. As discussed above with reference to the first sensor assembly 102 and second sensor assembly 108, the signal processing unit 114 is configured to determine placement of the intubation tube in the body of the patient in response to analyzing the acoustic and/or the electrical signals received from the single sensor assembly 152. Generally, the signal processing unit 114 is configured to analyze spectral components of the signal detected by the single sensor assembly 152 and determine whether a frequency of the spectral components of the signal are characteristic of sounds induced by ventilation via the intubation tube of airflow to the lung or the stomach of the patient. Such processes are discussed herein with reference to the first and second sensor assemblies 102 and 108.

In some implementations, the signal processing unit 114 is further configured to provide an instruction to relocate the single sensor assembly 152 responsive to the determination. For example, responsive to a determination that the placement of the intubation tube is proper, the signal processing unit 114 may provide a verbal or visual instruction to an operator of the system to relocate the single sensor assembly 152 to a second position. Instructions may include text, images, moving images, video, audio, or tones. In some implementations, relocating the single sensor assembly 152 includes relocating the single sensor assembly 152 at one of the third left intercostal region, the third right intercostal region, a sixth left intercostal region, a sixth right intercostal region, or a stomach region of the body of the patient, although the single sensor assembly 152 may be relocated to any position on the body of the patient. Responsive to repositioning the single sensor assembly 152, the signal processing unit 114 may re-perform the signal collection processes and analysis. This process may be repeated for a predetermined iteration of locations or for a predetermined time duration. The signal processing unit 114 may compare the amplitude or frequency of spectral components of the signal detected by the acoustic sensor 156 of the single sensor assembly 152 at a first placement with the amplitude or frequency of spectral components of a signal detected at a second placement, or further placement, to determine positioning of the of intubation tube within the patient.

Collection of data from the acoustic sensors can be controlled to account for artifact due to vibration such as vibration from vehicular motion, patients being transported on stretchers, or clinicians touching and moving a patient during treatment. In some implementations, the system 100 described above may be configured to have at least one air flow sensor coupled with the signal processing unit 114 and configured to measure air flow within the intubation tube 140, such as shown in FIG. 1B. The at least one air flow sensor 160 is configured to provide an automatic analysis gate to receive signals at the one or more acoustic sensors during particular circumstances of operation, such as when air flow is occurring. The signal processing unit 114 can be configured to analyze spectral components of the signal detected by one or more acoustic sensors responsive to detecting air flow through the intubation tube 140. In some implementations, the air flow sensor 160 uses the principles of a differential air flow sensor. As shown in FIG. 1B, the sensor 160 is placed approximately either at the proximal tip 170 or distal tip 172 of the intubation tube 140. Based on detection of air flow in the intubation tube 140, the signal processing unit 114 can be configured to initiate an analysis of the sounds from the one or more acoustic sensors (e.g., acoustic sensor 156), reducing (e.g., minimizing) effects of vibration artifact.

As discussed above, when confirming the placement of an intubation tube in standard clinical situations, a stethoscope is typically manually moved by the clinician to each location. Once moved, the clinician listens for breaths at each moment a ventilation is delivered. In these scenarios, each position may require from 5-10 seconds of listening per breath taken of the patient. This process is repeated at potentially five locations for potentially two breaths. Thus, in these scenarios, the practice of intubation tube placement confirmation can take up to 100 seconds.

In some implementations, the air flow sensor 160 can be used for intubation tube placement such that placement can be confirmed automatically and at all locations using fewer than five seconds. In some implementations, the placement can be confirmed in about 3-5 seconds.

In some implementations, the gating function may be generated by a user input from the operator of the intubation placement system (e.g., system 100). For example, via an interface of the signal processing unit 114 the operator may select a triggering operation to begin the processes described above (e.g., "Start Listening Now" softkey). Other examples of ventilation monitoring are described in U.S. patent application Ser. No. 14/109,519, titled "VENTILATION MONITORING", which is incorporated herein by reference in its entirety.

In some implementations, the gating function may be provided by transthoracic impedance of the one or more sensor assemblies and/or capnography (ETCO2) information.

In some implementations, one or more pressure sensors may be located in the intubation tube 140 and coupled with the signal processing unit 114. A first pressure sensor 162 is positioned at or near the proximal tip 170 of the intubation tube 140 and at least a second pressure sensor 164 is located at or near the distal tip 172 of the intubation tube 140. The first and second pressure sensors 162 and 164 are configured to measure absolute pressure within the intubation tube 140. By measuring the pressures at the proximal and distal ends relative to ambient pressures, as well as the timing between the onset of pressure waves along the intubation tube 140, the coupled signal processing unit 114 may determine the source of the air flow, such as whether the air flow is due to spontaneous breathing by the patient or due to bagging by the clinician or a ventilator. Other examples of ventilation monitoring are described in U.S. patent application Ser. No. 11/384218 titled "AUTOMATED RESUSCITATION DEVICE WITH VENTILATION SENSING AND PROMPTING", which is incorporated herein by reference in its entirety. In some implementations, the processes and analyses described above may initiate or execute responsive to analysis of a pressure differential between the first pressure sensor 162 and the second pressure sensor 164.

In some implementations, a first sensor assembly may be placed over the stomach and a second sensor assembly may be positioned at approximately at a sternal notch of the body of the patient. The second sensor assembly may contain a first acoustic sensor faced laterally such that the first acoustic sensor of the centrally located second sensor assembly preferentially senses the sounds from the right lung. Similarly, the second sensor assembly may contain a second acoustic sensor faced such that the second acoustic sensor of the centrally located second sensor assembly preferentially senses the sounds from the left lung. If the intubation tube is placed too deeply, the amplitude of acoustic sounds measured from the left and right sensors may not be balanced, and if the tube is placed too shallow in the trachea, the amplitudes of the left and right sensor outputs may be balanced with an attenuated amplitude, as compared to a properly located intubation tube. In some implementations, if the left and right amplitudes are imbalanced, the signal processing unit (e.g., signal processing unit 114) may prompt or instruct the operator of the intubation system to adjust the position of the intubation tube, such as to pull the tube out approximately 1 inch and test again. Using air flow measures from the air flow sensor 160, the amplitude of spectral components of the signal detected by the one or more acoustics sensors can be normalized to air flow so that as the operator delivers ventilation, multiple ventilations with the tube at different depths can be compared. In some implementations, the intubation tube placement having the largest amplitude that is still balanced can be chosen as the proper intubation tube placement.

Figure 2:
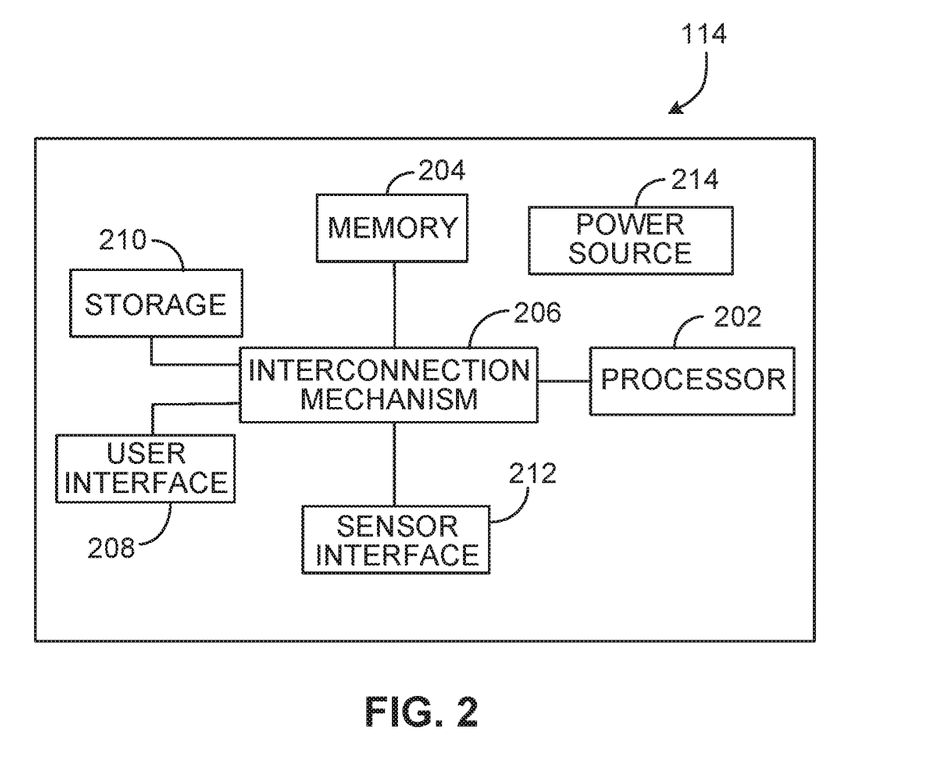
FIG. 2 shows a diagram of a signal processing system.

Referring to FIG. 2, there is illustrated a block diagram of a signal processing unit 114, in which various aspects and functions are practiced. As shown, the signal processing unit 114 can include one or more systems components that exchange information. More specifically, the signal processing unit 114 can include at least one processor 202, a power source 214, a data storage 210, a sensor interface 212, a user interface 208, a memory 204, and one or more interconnection mechanisms 206. The power source 214 may be a rechargeable battery that provides electrical power to other components. The at least one processor 202 may be any type of processor, multiprocessor, or controller. The at least one processor 202 is connected to the other system components, including one or more memory devices 204 by the interconnection mechanism 206.

The sensor interface 212 couples one or more sensor assemblies, such as the first and second sensor assemblies (102 and 108), to the at least one processor 202. In some implementations, the sensor interface 212 may also couple the at least one processor to other physiological sensors, such as activity sensors, pulse oxygen sensors, temperature sensors, respiratory rate sensors, thoracic impedance sensors, blood pressure sensors, acoustic sensors, etc. The sensor interface 212 can include signal processing circuitry, such as the circuitry discussed above.

The memory 204 stores programs (e.g., sequences of instructions coded to be executable by the processor 202) and data during operation of the signal processing unit 114. Thus, the memory 204 may be a relatively high performance, volatile, random access memory such as a dynamic random access memory ("DRAM") or static memory ("SRAM"). However, the memory 204 may include any device for storing data, such as a disk drive or other nonvolatile storage device. Various examples may organize the memory 204 into particularized and, in some cases, unique structures to perform the functions disclosed herein. These data structures may be sized and organized to store values for particular data and types of data.

Components of the signal processing unit 114 are coupled by an interconnection mechanism such as the interconnection mechanism 206. The interconnection mechanism 206 may include any communication coupling between system components such as one or more physical busses in conformance with specialized or standard computing bus technologies such as IDE, SCSI, PCI and InfiniBand. The interconnection mechanism 206 enables communications, including instructions and data, to be exchanged between system components of the signal processing unit 114.

The signal processing unit 114 can also include one or more user interface devices 208 such as input devices, output devices and combination input/output devices. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the signal processing unit 114 to exchange information and to communicate with external entities, such as users and other systems.

The data storage element 210 includes a computer readable and writeable data storage medium configured to store noon-transitory instructions and other data, and cant include both nonvolatile storage media, such as optical or magnetic disk, ROM or flash memory, as well as volatile memory, such as RAM. The instructions may include executable programs or other code that can be executed by the at least one processor 202 to perform any of the functions described here below.

In some implementations, the signal processing unit 114 includes additional components and/or interfaces, such as a communication network interface (wired and/or wireless), and the at least one processor 202 may include a power saving processor arrangement. In various implementations, the signal processing unit 114 may include a digital signal processor having architecture to measure, filter, and/or compress discrete or continuous analog signals received from the sensor assemblies.

As discussed above, use of a first and second sensor assembly, in addition to a signal processing unit, can improve the accuracy and safety of endotracheal intubation tube placement. The intubation tube placement system can discern an acoustic sound is indicative of esophageal or tracheal intubation tube placement for a user. In some implementations, the system reduces effects from environmental conditions, such as ambient noise, that may otherwise interfere with intubation tube placement determinations.

Figure 3:
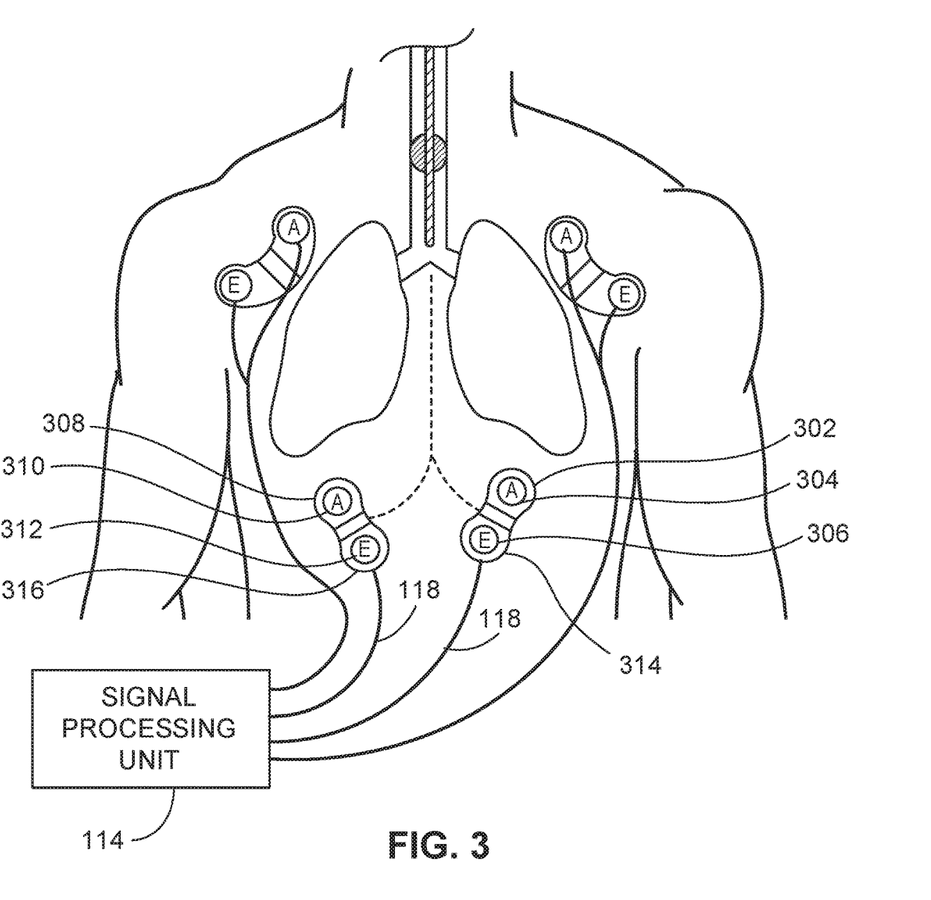
FIGS. 3-4 show examples of intubation tube placement systems.

FIG. 3 shows an example intubation tube placement system. With continuing reference to FIG. 1A and FIG. 2, in addition to a first sensor assembly and a second sensor assembly each having an acoustic sensor and an ECG electrode coupled to the body, some implementations can further include a third sensor assembly 302 having an acoustic sensor 304 and an ECG electrode 306, and a fourth sensor assembly 308 having an acoustic sensor 310 and an ECG electrode. In some implementations, the ECG electrodes are proximate and removably coupled to the third and fourth acoustic sensors, respectively. The third sensor assembly 302 is configured to be disposed at approximately the left abdominal region of the body and the fourth sensor assembly 308 is configured to be disposed at approximately the right abdominal region of the body. As shown in FIG. 3, the dispositions can include the area slightly above the diaphragm approximately at the sixth left and right intercostals. In some implementations, the sensors can be configured to be displaced in other regions of the patient's body.

Although various types of sensors may be employed, the acoustic sensor of the third sensor assembly 304 and the acoustic sensor of the fourth sensor assembly 310 can include an accelerometer or a microphone. The acoustic sensor is configured to convey acoustic signals, such as those created by activity (e.g., movement) of the lungs or stomach of the patient. The acoustic sensors are interconnected, via the connection element 118, with the signal processing unit 114 and may exchange data such as detected acoustic signals. In some implementations, the third sensor assembly 302 and the fourth sensor assembly 308 include a self-adhesive pad (shown as 314 and 316) for traction against the patient's body. The self-adhesive pad stabilizes the respective sensor assembly against the patient and prevents movement during the course of the intubation process.

As discussed above with reference to FIG. 1A, signals from the body detected by the acoustics sensors can be received by the signal processing unit 114. In addition to determining placement of the intubation tube in the body of the patient in response to analyzing the acoustic signals received from the first and second sensor assemblies, the signal processing unit can be further configured to determine tube placement in response to analyzing acoustic signals received from the third sensor assembly 302 and fourth sensor assembly 308. Accordingly, the signal processing unit 114 is configured to compare spectral components of the signals collected by the third and fourth sensor assemblies with a predetermined threshold to determine proper placement of the intubation tube in the trachea. In some implementations, the predetermined threshold can be the same predetermined threshold as discussed above with reference to the first sensor assembly 102 and the second sensor assembly 108. In some implementations, the predetermined threshold is unique to the third sensor assembly 302 and fourth sensor assembly 308.

Furthermore, the signal processing unit can be further configured to determine placement of the distal end of the intubation tube relative to the carina in response to analysis of the spectral components of the acoustic signals received from the third sensor assembly 302 and fourth sensor assembly 304. The signal processing unit 114 is configured to compare an amplitude of the spectral components of the signals received from the acoustic sensor of the third sensor assembly 302 to an amplitude of the spectral components of the signal received from the fourth sensor assembly 308. In some implementations, the signal processing unit 114 can also be configured to compare the amplitudes of spectral components of signals from acoustic sensors disposed on the same side of the patient's body. For example, the signal processing unit may compare amplitudes of signals received from a first sensor disposed proximate the third left intercostal region of the patient's body and a third sensor disposed proximate the sixth left intercostal region of the patient's body. The signal processing unit 114 is configured to determine displacement of the body of the patient from detected signal data provided by the third sensor assembly 302 and the fourth sensor assembly 308. The signal processing unit 114 is configured to determine whether a slow level DC component of displacement is occurring, and determine if the intubation tube has been properly placed. As described above, in some implementations, the signal processing unit 114 can be configured to convey proper placement of the intubation tube or convey an alert when the intubation tube has been improperly placed.

Figure 4:
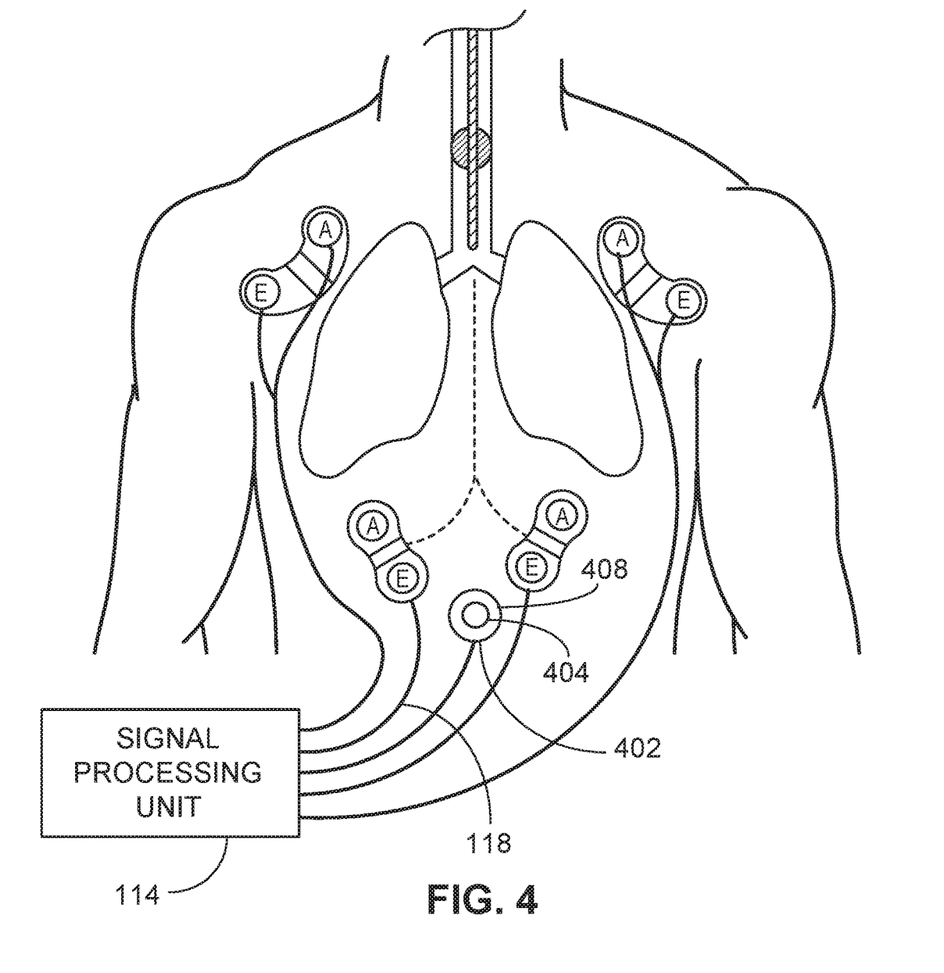

FIG. 4 shows an example of an intubation tube placement system. In addition to a first sensor assembly, a second sensor assembly, a third sensor assembly, and a fourth sensor assembly, each having an acoustic sensor and an ECG electrode, an implementation can further include a fifth sensor assembly 402 having an acoustic sensor 404. As shown in FIG. 4, the fifth sensor assembly 402 can be configured to be disposed at approximately the stomach region of the patient. Although various types of sensors may be employed, the acoustic sensor 404 of various implementations can include an accelerometer, a piezoelectric strain gauge or a microphone. The acoustic sensor 404 is configured to convey acoustic signals, such as those created by activity of the stomach of the patient. The acoustic sensor 404 is interconnected, via the connection element 118, with the signal processing unit 114 and may exchange data such as detected acoustic signals. In some implementations, the fifth sensor assembly 402 includes a self-adhesive pad 408 for traction against the patient's body. The self-adhesive pad 408 stabilizes the sensor assembly against the patient and prevents movement during the course of the intubation process.

Signals from the body collected by the acoustic sensor 404 of the fifth sensor assembly 402 can be received at the signal processing unit 114. In addition to determining placement of the intubation tube in the body of the patient in response to analyzing the acoustic and/or the electrical signals received from the first, second, third, and fourth sensor assemblies, the signal processing unit 114 can be further configured to determine tube placement in response receiving signals collected by the fifth sensor assembly 402. In some implementations, the signal processing unit is configured to compare spectral components of the signals collected by the fifth sensor assembly 402 to a predetermined threshold to determine proper placement of the intubation tube in the trachea. In some implementations, because the fifth sensor assembly 402 is can be positioned proximate the stomach of the patient, heightened activity in the stomach region following the intubation process can be recognized as indication of improper tube placement.

Furthermore, the signal processing unit 114 is configured to determine displacement of the patient's body based on signals collected by the fifth sensor assembly 402. In some implementations, because the fifth sensor assembly 402 can be positioned proximate the stomach of the patient, increased displacement in the stomach region following the intubation process can be recognized as indication of improper tube placement. In some implementations, the signal processing unit can be configured to convey proper placement of the intubation tube or convey an alert when the intubation tube has been improperly placed.

Figure 5:
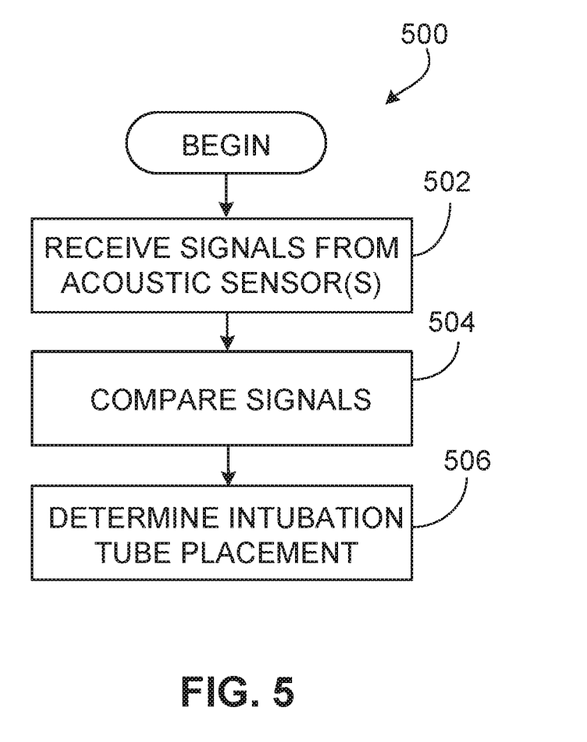
FIG. 5 shows an example of a process flow.

Referring now to FIG. 5, a method of determining intubation tube positioning in a patient, such as placement system 100 described above with reference to FIGS. 1-4, is shown. In step 502, method 500 can include receiving a first signal from a first acoustic sensor. In some implementations, the first acoustic sensor includes an accelerometer or a microphone. The acoustic sensor of an implementation is configured to collect and convey acoustic signals, such as those created by activity of the lungs or stomach of the patient. Prior to receiving the first signal from the first acoustic sensor, the method of FIG. 5 can further include placing the first acoustic sensor at approximately the third left intercostal region of the body of the patient. In some implementations, the first acoustic sensor is placed slightly above the nipple and below the clavicle. In some implementations, a signal processing unit, such as described above, is configured to guide placement of the first acoustic sensor. In some implementations in which only a single acoustic sensor is used, the signal processing unit may direct placement in the third left intercostal region of the body of the patient, followed by placement in the third right left intercostal region of the body of the patient, followed by placement in the sixth left intercostal region of the body of the patient, followed by placement in the sixth right intercostal region of the body of the patient, and also followed by placement in the stomach region of the patient. The signal processing may guide placement, of one or more sensor assemblies in any of the discussed areas or regions, in any particular order. In some implementations, if multiple acoustic sensors are used, for example, in the implementation described previously with reference to FIG. 4, the signal processing unit may direct placement of a first acoustic sensor in the third left intercostal region, followed by placement of a second acoustic sensor in the third right intercostal region, followed by placement of a third acoustic sensor in the sixth left intercostal region, followed by placement of a fourth acoustic sensor in the sixth right intercostal region, and also followed by placement of a fifth sensor in the stomach region of the patient.

In step 502, method 500 may also include receiving a second signal from a second acoustic sensor, receiving a third signal from a third acoustic sensor, receiving a fourth signal from a fourth acoustic sensor, and/or receiving a fifth signal from a fifth acoustic sensor. In some implementations, the second, third, fourth, and fifth acoustic sensor can each include an accelerometer or a microphone. The acoustic sensors are configured to detect and convey acoustic signals, such as those created by activity (e.g., movement) of the lungs or stomach of the patient. Prior to receiving the second, third, fourth, or fifth signal from the respective acoustic sensor, the method of FIG. 5 may further include placing the second, third, fourth, or fifth acoustic sensor.

In some implementations, act 502 may also include receiving a first ECG signal from a first ECG electrode removably coupled to the first acoustic sensor, receiving a second ECG signal from a second ECG electrode removably coupled to the second acoustic sensor, receiving a third ECG signal from a third ECG electrode removably coupled to the third acoustic sensor, and/or receiving a fourth ECG signal from a fourth ECG electrode removably coupled to the fourth acoustic sensor. In some implementations, the acoustic sensor and coupled ECG electrode may be symmetrically aligned with one another at spaced locations distributed on and along a shared detection axis, as described in U.S. Pat. No. 7,010,342, for example. In this regard, ECG signals that are collected by the ECG electrodes can be treated as emanating from the same source.

In some implementations, act 502 may include filtering the received signals prior to comparing and/or analyzing the signals. Step 502 may include low-pass filtering the received acoustic signal using a low-pass filter with a passband of 0 Hz to 5 Hz. In some implementations, act 502 may include band-pass filtering the first signal and the second signal prior to comparing the frequency of the spectral components of the first signal and the second signal to a determined threshold. The band-pass filter may include a filter with a passband of 5 Hz to 5000 Hz. In some implementations, act 502 can include low-pass filtering the received acoustic signals and band-pass filtering the received acoustic signals.

In step 504, various implementations of method 500 may include comparing a frequency of the spectral components of the received acoustic signals to a determined threshold. In some implementations the comparing includes comparing spectral components of the acoustic signals measured by the first and second sensor assemblies with spectral components of lung and esophageal sounds, since the sound of aspirating lungs is typically of a higher frequency than spectral components of stomach noises. The predetermined threshold is indicative of the discrepancy in lung and esophageal spectral components. In some implementations, the predetermined threshold can be determined based on patient age, gender, height, weight, and/or physical condition. Although primarily referred to as a discrete value, in additional implementations, the threshold value can include a range of frequencies.

In some implementations, method 500 may also include comparing an amplitude of spectral components of the first signal and the second signal. Because a properly placed intubation tube can evenly inflate each lung, substantially equal amplitudes of the signals collected by the first and second sensor assembly indicates that the tube has been properly positioned. Additionally, the signal processing unit may be configured to analyze the first and second signal and determine displacement of the body in the third left intercostal region and the third right intercostal region. Specifically, the signal processing unit may compare the displacement of the body in the third left intercostal region and the third right intercostal region.

Some implementations include comparing a frequency of the spectral components of the third signal and fourth signal, as well as amplitude of the spectral components of the third signal and fourth signal. The signal processing unit may be configured to analyze the third signal and the fourth signal, and determine displacement of the body in the left abdominal region and the right abdominal region. The signal processing unit may be configured to analyze spectral components of the third signal and the fourth signal, determine whether a frequency of the spectral components of the third signal and the fourth signal are above the determined threshold and an amplitude of the spectral components of the third signal and the fourth signal are substantially equal. In some implementations, the signal processing unit may also compare signals received from acoustic sensors on the same side of the patient's body (e.g., signals from sensors disposed proximate the third left intercostal and the sixth left intercostal). In some implementations, the signal processing structure may also be configured to analyze spectral components of the fifth signal.

In act 506, various implementations of the method 500 include determining endotracheal intubation tube placement. The signal processing unit may be configured to determine positioning of the intubation tube in the body of the patient in response to analysis of the comparison of the amplitude of spectral components, comparison of the frequency of the spectral components of the first and second signal, and displacement of the body. In some implementations, the method includes determining whether the intubation tube has been placed in the trachea or the esophagus, and determining if the distal end of the intubation tube has been inserted beyond the carina into the left or right lung, based on the comparison of the spectral components to the predetermined threshold and the comparison of spectral component amplitudes, and displacement of the body. If the spectral components exhibit a frequency component above the predetermined threshold, the signal processing unit can indicate to a user of the system that the intubation tube has been properly placed in the trachea. If the frequency characteristics of the spectral components fall below the predetermined threshold value, the signal processing unit can indicate, or convey an alert, that the intubation tube has been improperly placed, such as in the esophagus. Furthermore, if the received signals indicate heightened displacement in the patient's stomach, the signal processing unit can alert the user that the intubation tube is improperly placed, such as in the esophagus.

Some implementations can improve the accuracy and safety of conventional endotracheal intubation tube placement systems and techniques and discern whether an acoustic sound is indicative of esophageal or tracheal intubation tube placement. Furthermore, the system reduces the effects of environmental conditions, such as ambient noise, that may otherwise intubation adversely affect tube placement determinations.

Having thus described several aspects of at least various implementations of the systems and methods for intubation tube placement, it is to be appreciated various alterations, modifications, and improvements will readily occur to those skilled in the art. Such alterations, modifications, and improvements are intended to be part of this disclosure, and are intended to be within the scope of the systems and methods for intubation tube placement. Accordingly, the foregoing description and drawings are by way of example only.

Moreover, it is to be understood that both the foregoing description and information merely illustrative examples of various aspects and implementations the methods and systems for positioning an intubation tube, and are intended to provide an overview or framework for understanding the nature and character of the claimed aspects and implementations.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and implementations.

What is claimed is:

1. A system for determining positioning of an intubation tube in a patient, comprising:
    an intubation tube;
    at least one acoustic sensor configured to provide an acoustic sensor output indicative of acoustic vibration of the patient;
    and
    a signal processor configured to:
        provide a first instruction to position the at least one acoustic sensor at a first location of the patient;
        receive a first acoustic sensor output indicative of acoustic vibration at the first location of the patient;
        analyze spectral components of the first acoustic sensor output from the first location of the patient to estimate whether a frequency of the spectral components is characteristic of sounds induced by ventilation, via the intubation tube, of airflow to a lung or stomach of the patient;
        provide a second instruction to position the at least one acoustic sensor from the first location of the patient to a second location of the patient;
        receive a second acoustic sensor output indicative of acoustic vibration at the second location of the patient;
        analyze spectral components of the second acoustic sensor output from the second location of the patient to estimate whether a frequency of the spectral components is characteristic of sounds induced by ventilation, via the intubation tube, of airflow to a lung or stomach of the patient;
        determine a positioning of the intubation tube in the patient based on the analyzed spectral components of the first acoustic sensor output from the first location and of the second acoustic sensor output from the second location; and
        provide an indication of the determined positioning of the intubation tube in the patient.

2. The system of claim 1, wherein the indication of the determined positioning of the intubation tube in the patient comprises a signal indicative of proper placement of the intubation tube, and wherein the signal processor is configured to provide a notice indicative of proper placement of the intubation tube in response to receiving the signal.

3. The system of claim 2, wherein the notice indicative of proper placement of the intubation tube is provided in response to the signal processor determining that the intubation tube is placed in a trachea of the patient.

4. The system of claim 1, wherein the indication of the determined positioning of the intubation tube in the patient comprises a signal indicative of improper placement of the intubation tube, and wherein the signal processor is configured to provide an alert indicative of improper placement of the intubation tube.

5. The system of claim 4, wherein the alert indicative of improper placement of the intubation tube provided in response to the signal processor determining that the intubation tube is placed in an esophagus of the patient.

6. The system of claim 1, wherein the first instruction, the second instruction, or both the first and second instructions each comprises an audio instruction indicating a position on the patient for placement for the at least one acoustic sensor.

7. The system of claim 1, wherein the first instruction, the second instruction, or both the first instruction and the second instruction each comprises a visual instruction indicating a position on the patient for placement for the at least one acoustic sensor.

8. The system of claim 1, wherein the second location on the patient comprises one of a third left intercostal region, a third right intercostal region, a sixth left intercostal region, a sixth right intercostal region, or a stomach region of the patient.

9. The system of claim 1, wherein the signal processor is configured to:
    determine that the at least one acoustic sensor has been repositioned from the second location to an updated location;
    analyze spectral components of a third acoustic sensor output from the updated location of the patient to estimate whether a frequency of the spectral components is characteristic of sounds induced by ventilation, via the intubation tube, of airflow to a lung or stomach of the patient; and
    determining the positioning of the intubation tube in the patient based on the analyzed spectral components of the third acoustic sensor output from the updated location.

10. The system of claim 1, wherein the signal processor is configured to provide additional instructions to relocate the at least one acoustic sensor to each of a predetermined set of locations on the patient until the signal processor determines the positioning of the intubation tube in the patient based on analyzing an additional sensor output associated with each location of the predetermined set of locations.

11. The system of claim 1, wherein the at least one acoustic sensor comprises a first acoustic sensor and a second acoustic sensor; and wherein the signal processor is configured to provide instructions to relocate both the first acoustic sensor and the second acoustic sensor from respective first positions on the patient to respective second positions on a patient in response to determining the positioning of the intubation tube in the patient.

12. The system of claim 11, wherein the first acoustic sensor is configured to be placed over the stomach of the patient for a first position of the first acoustic sensor, and wherein the second acoustic sensor is configured to be placed at a sternal notch of the patient for a first position of the second acoustic sensor.

13. The system of claim 1, wherein the at least one acoustic sensor comprises, a microphone, a piezoelectric strain gauge, or an accelerometer.

14. The system of claim 1, wherein the at least one acoustic sensor comprises an accelerometer, and wherein the accelerometer is configured to provide a sensor output indicative of a position of the at least one acoustic sensor on the patient.

15. The system of claim 14, wherein the signal processor is configured to:

analyze the sensor output indicative of the position of the at least one acoustic sensor on the patient; and provide an indication of whether the accelerometer is correctly or incorrectly positioned on the patient.

16. The system of claim 1, comprising an electrocardiogram electrode, wherein the signal processor is configured to provide a third instruction to relocate the electrocardiogram electrode from a first electrocardiogram position on the patient to a second electrocardiogram position on a patient.

17. The system of claim 16, wherein the electrocardiogram electrode is coupled to the at least one acoustic sensor.

18. The system of claim 1, wherein the signal processor is configured to guide placement of the at least one acoustic sensor by providing the first instruction for placement of the at least one acoustic sensor at the first location prior to determining the positioning of the intubation tube in the patient.

19. The system of claim 1, wherein the signal processor is configured to compare received acoustic sensor outputs from two or more acoustic sensors; and provide an instruction to relocate at least one of the two or more acoustic sensors from a first location on the patient to a second location on the patient in response to comparing of the received acoustic sensor outputs from the two or more acoustic sensors.

20. The system of claim 1, comprising an airflow sensor configured to measure air flow within the intubation tube, wherein the signal processor is configured to determine the positioning of the intubation tube in the patient in response to receiving a signal, from the airflow sensor, indicative of the air flow within the intubation tube.

* * * * *